United States Patent
Komiyama et al.

(10) Patent No.: US 6,900,439 B2
(45) Date of Patent: May 31, 2005

(54) GAS LEAKAGE DETECTION SYSTEM, GAS LEAKAGE DETECTION METHOD AND SEMICONDUCTOR MANUFACTURING APPARATUS

(75) Inventors: Kiyoshi Komiyama, Nirasaki (JP); Shinichi Watanabe, Nirasaki (JP); Kazunori Gotoda, Yokohama (JP)

(73) Assignees: Tokyo Electron Limited, Tokyo (JP); Tomoe Shokai Co., Ltd., Tokyo (JP)

( * ) Notice: Subject to any disclaimer, the term of this patent is extended or adjusted under 35 U.S.C. 154(b) by 206 days.

(21) Appl. No.: 10/204,322

(22) PCT Filed: Feb. 23, 2001

(86) PCT No.: PCT/JP01/01378

§ 371 (c)(1),
(2), (4) Date: Aug. 21, 2002

(87) PCT Pub. No.: WO01/63250

PCT Pub. Date: Aug. 30, 2001

(65) Prior Publication Data

US 2003/0010918 A1 Jan. 16, 2003

(30) Foreign Application Priority Data

Feb. 24, 2000 (JP) ............................ 2000-047796

(51) Int. Cl.[7] ................................................ G01J 5/02
(52) U.S. Cl. ......................... 250/338.08; 250/338.07; 356/51
(58) Field of Search ....................... 250/339.08, 339.07, 250/339.06, 339.01, 338.1, 336.1, 339.13, 341.1, 343; 356/51

(56) References Cited

U.S. PATENT DOCUMENTS

| | | | |
|---|---|---|---|
| 5,811,812 A | * | 9/1998 | Williams et al. ............ 250/343 |
| 5,892,586 A | | 4/1999 | Thony et al. |
| 6,157,033 A | * | 12/2000 | Chudnovsky ............ 250/338.5 |
| 6,240,610 B1 | * | 6/2001 | Ishihara et al. ............ 29/25.01 |
| 2004/0103715 A1 | * | 6/2004 | Liu et al. ..................... 73/40.7 |

FOREIGN PATENT DOCUMENTS

| | | | | |
|---|---|---|---|---|
| JP | 05052754 | | 3/1993 | |
| JP | 05099778 A | * | 4/1993 | ............ G01M/3/04 |
| JP | 05099781 A | * | 4/1993 | ............ G01M/3/26 |
| JP | 06307967 | | 4/1994 | |
| JP | 06323944 | | 11/1994 | |
| JP | 07292408 | | 11/1995 | |
| JP | 10-30983 | | 2/1998 | |
| JP | 10185813 | | 7/1998 | |
| JP | 11118712 | | 4/1999 | |

OTHER PUBLICATIONS

Clean Technology, vol. 7, No. 7 (JAPAN), Nippon Kogoyo Shuppan, Jul., 1997, pp. 1–3.

Clean Technology, vol. 4, No. 5, (JAPAN) Nippon Kogyo Shuppan, May, 1994, pp. 54–59.

* cited by examiner

Primary Examiner—David Porta
Assistant Examiner—Christine Sung (57) ABSTRACT

Components of sampled gases are analyzed by a Fourier transform infrared spectrophotometer 28. It is determined whether or not the analyzed gases include at least one kind of specific gases equal to or more than a predetermined quantity. In a case where mixed gases include at least one kind of the specific gases equal to or more than the predetermined quantity, a controller 30 supplies an operation display monitor 31 with a signal indicating leakage of the kind of the specific gases. Hence, it is possible to realize detection by kind of the gases with high accuracy irrespective of the kind of leaked gas.

29 Claims, 8 Drawing Sheets

GAS LEAKAGE DETECTION SYSTEM, GAS LEAKAGE DETECTION METHOD AND SEMICONDUCTOR MANUFACTURING APPARATUS

This application is the National Phase of International Application PCT/JP01/01378 filed Feb. 23, 2001 which designated the U.S. and that International Application was not published under PCT Article 21(2) in English.

TECHNICAL FIELD

The present invention generally relates to gas leakage detection technologies, and more particularly to a gas leakage detection system, a gas leakage detection method and a semiconductor apparatus having a gas detection system that detect leakage of a plurality of kinds of gases.

BACKGROUND ART

Figure 1:
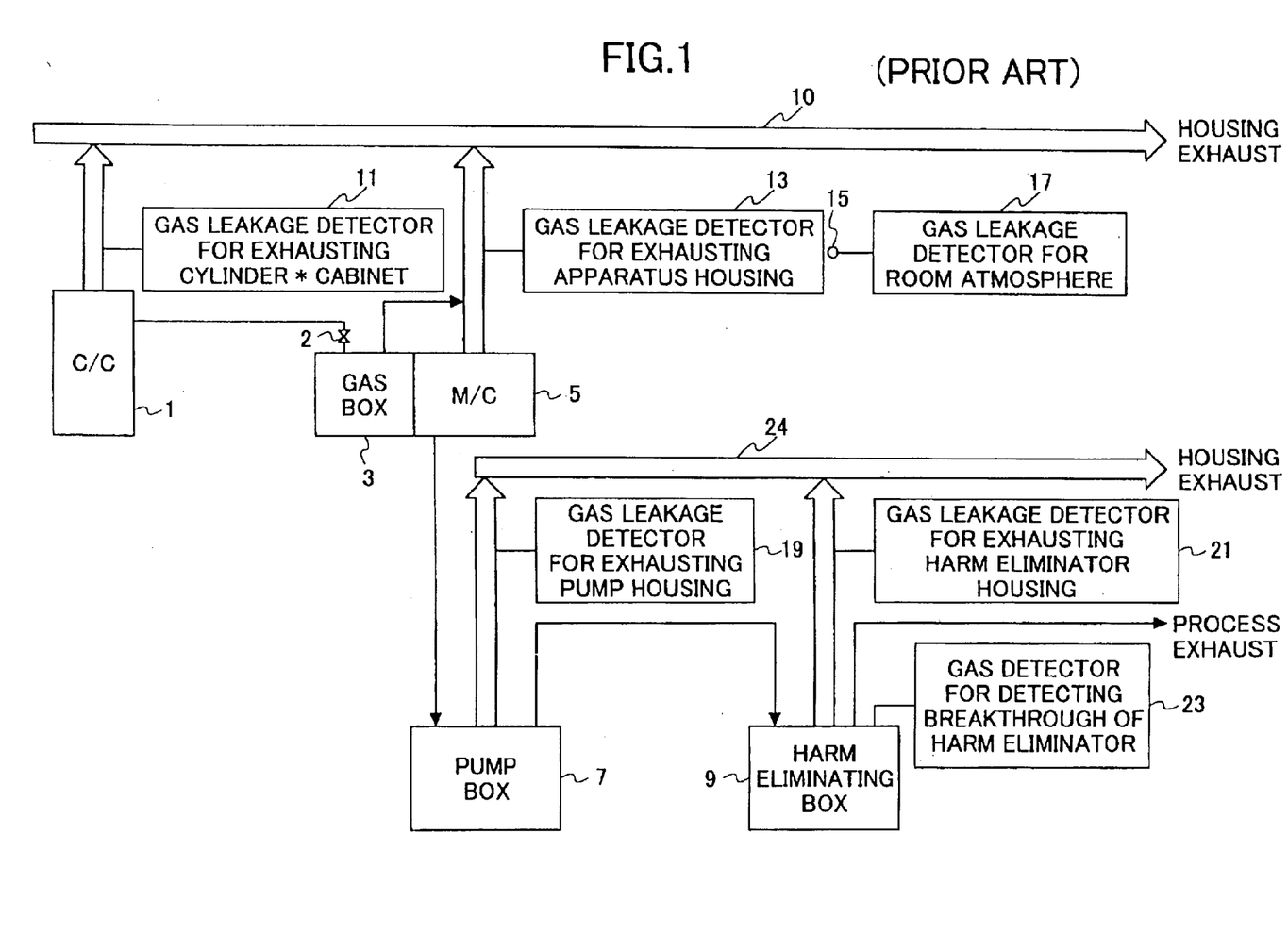
FIG. 1 is a block diagram of a conventional gas leakage detection system.

FIG. 1 is a block diagram of a conventional gas leakage detection system. As shown in FIG. 1, the conventional gas leakage detection system includes a cylinder cabinet (C/C) 1 that receives a cylinder, a gas box 3 that controls flow rate and the like of gas supplied to a process chamber of a semiconductor manufacturing apparatus, a semiconductor manufacturing apparatus housing (M/C) 5 that has the process chamber of the semiconductor manufacturing apparatus, a pump box 7 that has a vacuum pump, a harm eliminating box 9 that has a harm eliminator, exhaust pipes 10 and 24, a gas leakage detector 11 for exhausting a cylinder cabinet housing, a gas leakage detector 13 for exhausting an-apparatus housing, a gas sampling part 15, a gas leakage detector 17 for room atmosphere, a gas leakage detector 19 for exhausting a pump housing, a gas leakage detector 21 for exhausting a harm eliminator housing, and a gas detector 23 for detecting the breakthrough of the harm eliminator.

The cylinder cabinet (C/C) 1 is connected to the exhaust pipe 10, and the gas leakage detector 11 for exhausting the cylinder cabinet housing is connected between the cylinder cabinet (C/C) 1 and the exhaust pipe 10. A gas connecting port of the gas box 3 is connected to the cylinder cabinet (C/C) 1 via a stop valve 2. In addition, an exhaust opening of the gas box 3 is connected to the exhaust pipe 10. The semiconductor manufacturing apparatus housing (M/C) 5 is connected to the exhaust pipe 10. The gas leakage detector 13 for exhausting the apparatus housing is connected between the gas box 3 and the semiconductor manufacturing apparatus housing (M/C) 5, and the exhaust pipe 10.

A vacuum pump admission port of the pump box 7 is connected to the semiconductor manufacturing apparatus housing (M/C) 5, and an exhaust opening is connected to the exhaust pipe 24. The gas leakage detector 19 for exhausting the pump housing is connected between the pump box 7 and the exhaust pipe 24. Additionally, a vacuum pump exhaust connecting port of the harm eliminating box 9 is connected to the vacuum pump of the pump box 7. A harm eliminating box housing exhaust is connected to the exhaust pipe 24, and the gas leakage detector 21 for exhausting the harm eliminator housing is connected between the harm eliminating box 9 and the exhaust pipe 24. Process exhaust is performed from an exhaust opening of the harm eliminator of the harm eliminating box 9. The gas detector 23 for detecting the breakthrough of the harm eliminator is connected to the exhaust opening of the harm eliminator. The gas sampling port (sample port) 15 is arranged in a room where the gas leakage detection system is installed, and the gas leakage detector 17 for the room atmosphere is connected to the gas sampling port 15. Each of the above-mentioned gas leakage detectors is arranged at each detecting place as many as the number of the kinds of gases that are to be detected at the detecting place. Further, the housing exhaust is performed through the above-mentioned exhaust pipes 10 and 24.

In a conventional system including a semiconductor manufacturing apparatus that consumes a flammable gas and a toxic gas in a manufacturing process of a semiconductor circuit, generally, a place having a possibility of leaking gas, such as a housing covering a process chamber, is forcibly exhausted, and at the same time, gas leakage detection alarm equipment corresponding to the kind of a gas in danger of leaking is installed at a vacuum port.

In addition, generally, the gas leakage detection alarm equipment is installed also in a harm eliminator provided to a semiconductor manufacturing apparatus system. That is, since the harm eliminator is filled with a medical agent for eliminating a harmful substance in an exhaust gas, the gas leakage detection alarm equipment is installed also for detecting a breakthrough point. The breakthrough point refers to a point where the medical agent that absorbs and eliminates a harmful substance is saturated and not able to abate the harmful substance any more.

Further, generally, it is difficult for a current gas leakage detector and a current breakthrough detector to detect a gas that is stable and hard to be decomposed. Thus, a secondary detection or the like in which detection is performed after heat decomposition occurs, is performed on gases such as PFC, $NF_3$ and the like. The breakthrough detector in the harm eliminator samples a gas mainly from a dry atmosphere. Accordingly, there is a problem in that the breakthrough detector may not be able to detect a kind of a gas that is to be detected after hydrolysis is performed.

Further, as gases that are to be detected after hydrolysis is performed, there are $WF_6$, $BCl_3$, $SiH_2Cl_2$ and the like. $WF_6$ is detected after generating HF by hydrolysis, and $SiH_2Cl_2$ is detected after generating HCl in a similar manner.

Additionally, in the detection of gas leakage in a dry atmosphere as mentioned above, there is another problem in that a stable operation is difficult since an internal liquid of a sensor that is included in the breakthrough detector decreases significantly.

Furthermore, as for the entire conventional semiconductor manufacturing apparatus system using many kinds of gases, there is another problem in that there are many control items since, as mentioned above, the gas leakage detection alarm equipment is required for each kind of gas that is a detection object.

Additionally, in the above-mentioned gas leakage detection alarm equipment, there is another problem in that labor hours and management expenses increase, since not only checks such as a daily check, a periodic calibration and an alarm test are required, but also the number of control items reaches several hundred in a factory manufacturing semiconductor circuits.

In these days, along with the diversification of the kinds of gases used in the semiconductor manufacturing system, new kinds of gases are also developed. However, the development of the corresponding gas detector has not caught up yet, and data of an interference gas similar to a gas that is the detection object have not been sufficiently obtained. Accordingly, in the conventional gas detector, there is another problem in that various unexpected problems may occur.

In addition, the $SiH_4$ detector and the $CiF_3$ detector can detect a plurality of gases with a single detector. Such detection is called representative detection and has an advantage in that a single detector can detect the kinds of gases that have coherency. In other words, the $SiH_4$ detector can detect hydrides such as $SiH_4$, $PH_3$, $Si_2H_6$, $B_2H_6$ and $ASH_3$, and the $CiF_3$ detector can detect halogenides such as $CiF_3$, $Cl_2$, HCl, HF and $BCl_3$, and $O_3$.

However, in the above-mentioned representative detection, it is impossible to selectively detect kinds of gases and to specify the kinds of gases that are detected. Additionally, since the gases that are targets of the representative detection have a property of easily reacting to an oxidant, $NO_x$ and the like included in the air, there is another problem in that detecting leakage of the gases is subject to interference by the air. Further, the acceptable concentration differs depending on the kind of a gas that is the detection target. However, only one reference set value can be set for determining leakage. Thus, there is another problem in that it is difficult to set the set value.

DISCLOSURE OF THE INVENTION

It is a general object of the present invention to provide an improved and useful gas leakage detection system and a gas leakage detection method in which the above-mentioned problems are eliminated.

A more specific object of the present invention is to provide a gas leakage detection system and a gas leakage detection method that can perform detection for each kind of gases with high accuracy irrespective of the kind of leaking gas.

In order to achieve the above-mentioned objects, according to one aspect of the present invention, there is provided a gas leakage detection system detecting leakage of a plurality of kinds of specific gases including: analyzing means for analyzing components of a sampled gas; and determining means for determining that at least one kind of the specific gases leaks when the one kind of the specific gases is included in the sampled gas equal to or more than the predetermined quantity, as a result of analysis by the analyzing means.

According to the above-mentioned invention, it is possible for the analyzing means to detect the leakage of a plurality of specific gases by type with good accuracy.

The gas leakage detection system according to the present invention includes sampling means for sampling gases exhausted from harm eliminating means for eliminating a harmful substance included in the plurality of kinds of specific gases. At the same time, the determining means may determine that the harm eliminating means is abnormal, in a case where the harmful substance is included in the gases exhausted from the harm eliminating means equal to or more than a predetermined quantity. Hence, it is possible to detect the breakthrough point of the harm eliminating means with good accuracy. In addition, the analyzing means can be a Fourier transform infrared spectrophotometer.

Additionally, the above-mentioned gas leakage detection system may further include nitrogen gas supplying means for introducing nitrogen gas into the Fourier transform infrared spectrophotometer for zero calibration of the Fourier transform infrared spectrophotometer; and controlling means for controlling the nitrogen gas supplying means so that the zero calibration is performed at predetermined intervals. According to such means, it is possible to maintain the accuracy of the analysis by the Fourier transform infrared spectrophotometer.

The gas leakage detection system according to the present invention may include sampling means for individually sampling gases from a plurality of sampling locations, and may successively supply sampled gases to the analyzing means. In addition, the gas leakage detection system according to the present invention may include sampling means for individually sampling gases from the plurality of sampling locations; and controlling means for controlling the gases sampled from the plurality of sampling locations to be individually and successively supplied to the analyzing means, in a case where at least one kind of the specific gases is included in the gas equal to or more than a predetermined quantity, as a result of the analysis by the analyzing means, when the gases sampled from the plurality of sampling locations are simultaneously supplied to the gas analyzing means. Hence, it is possible to specify the place where the specific gas is leaking.

Additionally, the sampling means may include a flow rate regulating means for regulating the flow rate of a gas flowing from at least one of the sampling locations to the analyzing means. Hence, it is possible to increase the accuracy of the analysis by the analyzing means. Further, alarming means for raising an alarm, when the gas is supplied to the analyzing means at a flow rate beyond a predetermined range, may be further included. According to such means, it is possible to maintain the accuracy of the analysis by the analyzing means.

Additionally, diluting means may be further included for diluting a predetermined kind of the specific gases exhausted from the analyzing means, in a case where the predetermined kind of the specific gases is included in the sampled gas equal to or more than the predetermined quantity, as a result of the analysis by the analyzing means. According to such a means, it is possible to avoid the risk of the specific gases.

Further, the determining means may output a signal indicating leakage of one kind of the specific gases determined to be leaking, when determining that at least one kind of the specific gases leaks. Hence, it is possible to transmit a signal indicating the leakage to an upper machine such as a host computer, for example.

In addition, the determining means may output a signal indicating that the harm eliminating means is abnormal, when determining that the harm eliminating means is abnormal. Hence, it is possible to transmit a signal indicating the abnormality of the harm eliminating means to an upper machine such as a host computer, for example.

Furthermore, according to another aspect of the present invention, there is provided a gas leakage detection method of detecting leakage of a plurality of kinds of specific gases including: an analyzing step of analyzing components of sampled gases; a step of determining whether or not at least one kind of the specific gases is included in the sampled gases equal to or more than a predetermined quantity; and a step of determining that one kind of the specific gases leaks, in a case where it is determined that at least the one kind of the specific gases is included equal to or more than the predetermined quantity.

According to another aspect of the present invention, there is provided a gas leakage detection method of monitoring an operating state of a harm eliminating means eliminating a harmful substance included in a plurality of kinds of specific gases that leak including: an analyzing step of analyzing components of gases exhausted from the harm eliminating means; a step of determining whether or not the gases exhausted from the harm eliminating means include at least one kind of the specific gases equal to or more than a predetermined quantity; and a step of determining that abnormality occurs in the harm eliminator, in a case where it is determined that the gases exhausted from the harm eliminating means include at least one kind of the specific gases equal to or more than the predetermined quantity.

In the gas leakage detection method of the present invention, the analysis of the components included in the gases can be performed by a Fourier transform infrared spectrophotometer.

Additionally, it is possible to perform zero calibration of the Fourier transform infrared spectrophotometer at predetermined intervals, and at the same time, to supply nitrogen gas to the Fourier transform infrared spectrophotometer in the zero calibration.

Further, the components of the gases sampled at a plurality of sampling locations may be successively analyzed. In addition, as a result of the analysis, in a case where the sampled gases include at least one of the specific gases equal to or more than the predetermined quantity, it is possible to perform the analysis by individually and successively selecting the sampling locations of the gases. Here, it is possible to arbitrarily regulate the quantity of the gases that are targets of the analysis.

Furthermore, an alarm may be raised when the flow rate of the gases to be analyzed exceeds a predetermined value. In a case where the gases include the predetermined specific gas equal to or more than a predetermined quantity as a result of the analysis, the predetermined specific gas exhausted after the analysis may be diluted.

In addition, according to another aspect of the present invention, there is provided a semiconductor manufacturing apparatus incorporating the above-mentioned gas leakage detection system.

Other objects, features and advantages of the present invention will become more apparent from the following detailed description when read in conjunction with the accompanying drawings.

BEST MODE FOR CARRYING OUT THE INVENTION

In the following, a description will be given of embodiments of the present invention, by referring to the drawings.

It should be noted that, in the drawings, those corresponding components are designated by the same reference numerals.

Figure 2:
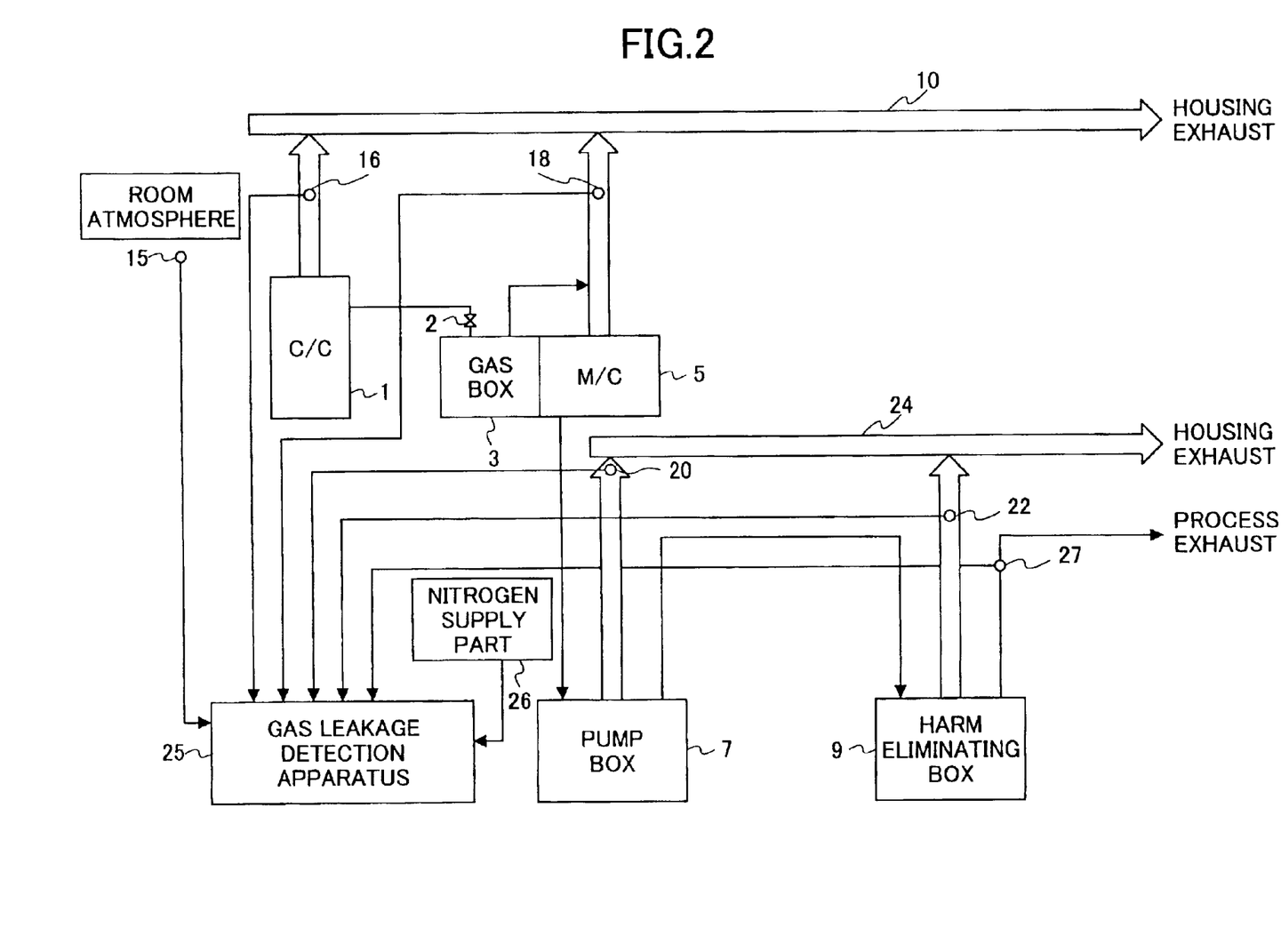
FIG. 2 is a general block diagram of a gas leakage detection system according to the present invention.

FIG. 2 is a general block diagram of a gas leakage detection system according to the present invention. As shown in FIG. 2, the gas leakage detection system according to the present invention is different from the conventional gas leakage detection system shown in FIG. 1 in that the gas leakage detector 11 for exhausting the cylinder cabinet housing, the gas leakage detector 13 for exhausting the apparatus housing, the gas leakage detector 17 for the room atmosphere, the gas leakage detector 19 for exhausting the pump housing, the gas leakage detector 21 for exhausting the harm eliminator housing and the gas detector 23 for detecting the breakthrough of the harm eliminator are eliminated, and a gas leakage detection apparatus 25 is newly provided instead.

In addition, differences exist in the following aspects. That is, the gas sampling port (sample port) 15 and a nitrogen supply part 26 are connected to the gas leakage detection apparatus 25. Further, a sample port 16 is provided to a pipe connecting the cylinder cabinet 1 and the exhaust pipe 10. Additionally, a sample port 18 is provided to a pipe connecting the semiconductor manufacturing apparatus housing 5 and the exhaust pipe 10. Furthermore, a sample port 20 is provided to a pipe connecting the pump box 7 and the exhaust pipe 24. A sample port 22 is provided to a pipe connecting the harm eliminating box 9 and the exhaust pipe 24. A sample port 27 is provided to an exhaust opening of the harm eliminating box 9. Then, each of the above-mentioned sample ports 16, 18, 20, 22 and 27 is connected to the gas leakage detection apparatus 25 via an aspiration pipe such as a teflon tube.

[First Embodiment]

Figure 3:
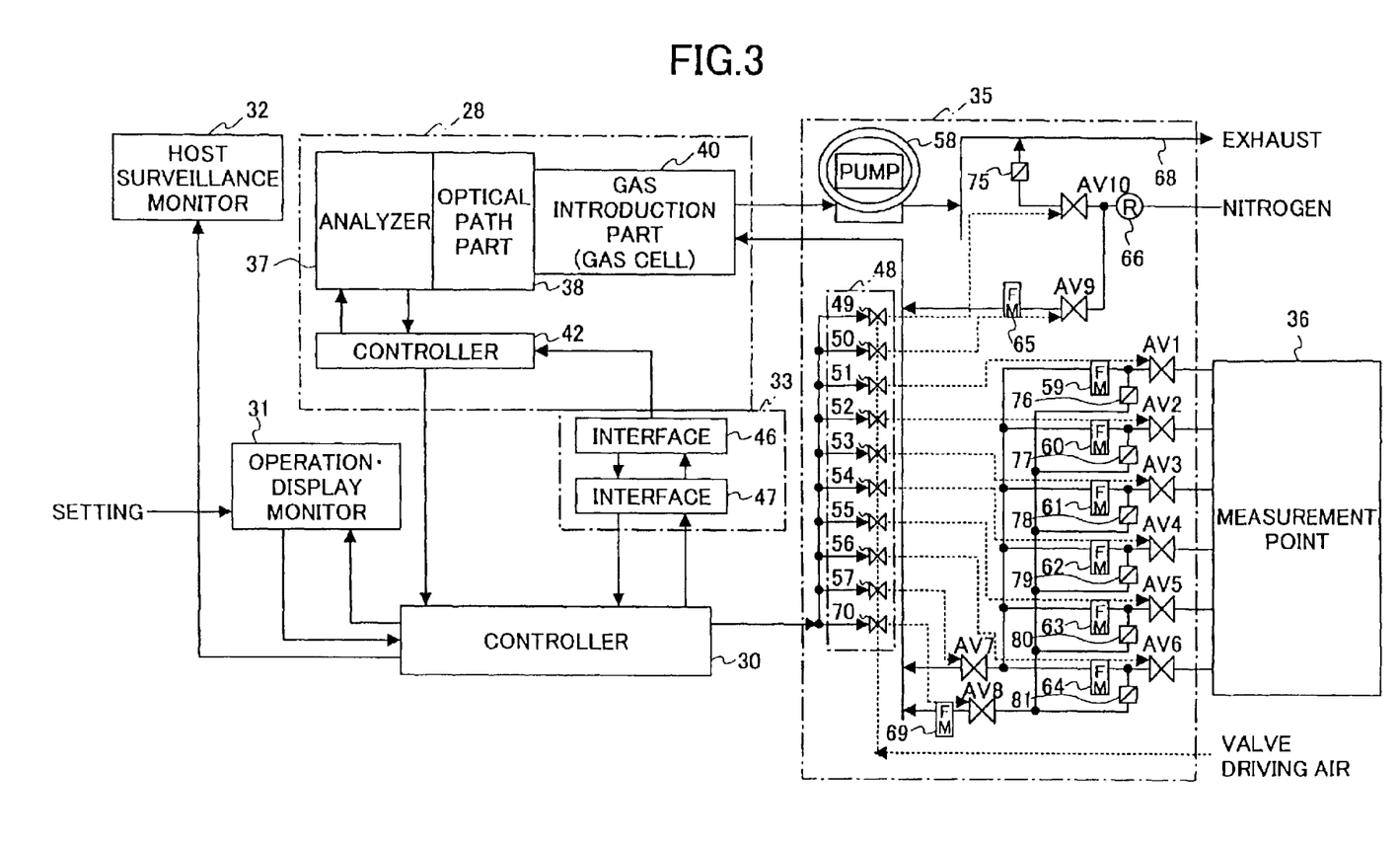
FIG. 3 is a block diagram of a gas leakage detection apparatus provided to a gas leakage detection system according to a first embodiment of the present invention.

FIG. 3 is a block diagram of a gas leakage detection apparatus installed in a gas leakage detection system according to a first embodiment of the present invention. As shown in FIG. 3, the gas leakage detection apparatus 25 includes a Fourier transform infrared spectrophotometer 28, a controller 30, an operation display monitor 31, an additional function part 33 and a valve switch part 35. A measurement point 36 and a nitrogen supply part 26 are connected to the valve switch part 35. Further, the measurement point 36 includes the sample ports 15, 16, 18, 20 and 22 that are shown in FIG. 2.

The Fourier transform infrared spectrophotometer 28 includes an analyzer 37, an optical path part 38, a gas introduction part (gas cell) 40 and a controller 42. The controller 42 is connected to the analyzer 37. In addition, the controller 42 stores spectra of gases that are the detection targets beforehand, and compares a spectrum of a gas that is introduced into the gas cell 40 with the stored spectra.

The additional function part 33 includes interfaces 46 and 47. The interface 46 is connected to the controller 42. The interface 47 is connected between the interface 46 and the controller 30. Additionally, the controller 30 is connected to the operation display monitor 31, a host surveillance monitor 32 and the controller 42.

The valve switch part 35 includes a magnet valve unit 48, a pump 58, flowmeters 59 through 65 and 69, a pressure regulator 66, air driving valves AV1 through AV10, and check valves 75 through 81. The magnet valve unit 48 is provided with magnet valves 49 through 57 and 70 that open/close according to a valve switch signal supplied from the controller 30. In addition, the air driving valves AV1 through AV10 can be arbitrarily opened and closed according to the pressure of valve operation air that is supplied. Further the check valve 75 is connected between the air driving valve AV10 and an exhaust pipe 68. Additionally, the check valves 76 through 81 are connected between the air driving valve AV8 and the air driving valves AV1 through AV6, respectively.

The pump 58 and the air driving valve AV7 are connected to the gas cell 40. In addition, the air driving valve AV8 is also connected to the gas cell 40 via the flowmeter 69. The flowmeters 59 through 64 are connected to the air driving valve AV7 Then, the flowmeters 59 through 64 are connected to corresponding air driving valves AV1 through AV6 one by one.

Further, the flowmeter 65 is connected to the gas cell 40, and the air driving valve AV9 is connected to the flowmeter 65. Then, the check valve 75 and the air driving valve AV10 are serially connected to the exhaust pipe 68 that is connected to an exhaust opening of the pump 58. Further, both air driving valves AV9 and AV10 are connected to the pressure regulator 66.

On the other hand, air for driving valves is supplied to the magnet valves 49 through 57 and 70. At the same time, the air for driving valves is provided from the magnet valves 49 through 57 and 70 to the corresponding air driving valves AV1 through AV10. In addition, the check valves 75 and 76 through 81 are equipped for avoiding back flow of gases.

Next, a description will be given of the operation of the gas leakage detection system according to this embodiment having the construction as mentioned above, by referring to a flow chart shown in FIG. 4.

In the gas leakage detection system according to this embodiment, the power is turned ON and all the air driving valves AV1 through AV10 are closed by the controller 30 in an initial state. Additionally, the pump 58 is turned OFF, and a manual mode in which all operations are manually performed is set.

First, the pump 58 is operated. When the controller 42 supplies the controller 30 with a signal indicating that measurement preparation of the Fourier/transform infrared spectrophotometer 28 is completed, the controller 30 determines whether to set the gas leakage detection system in an automatic mode or in the manual mode based on a setpoint signal supplied from the operation display monitor 31. It should be noted that the automatic mode refers to a mode in which the following process is automatically carried out according to sequence control.

Next, a description will be given of the operation when set in the above-mentioned automatic mode, by referring to FIG. 4. It should be noted that the following operation can be carried out in the manual mode.

Figure 4:
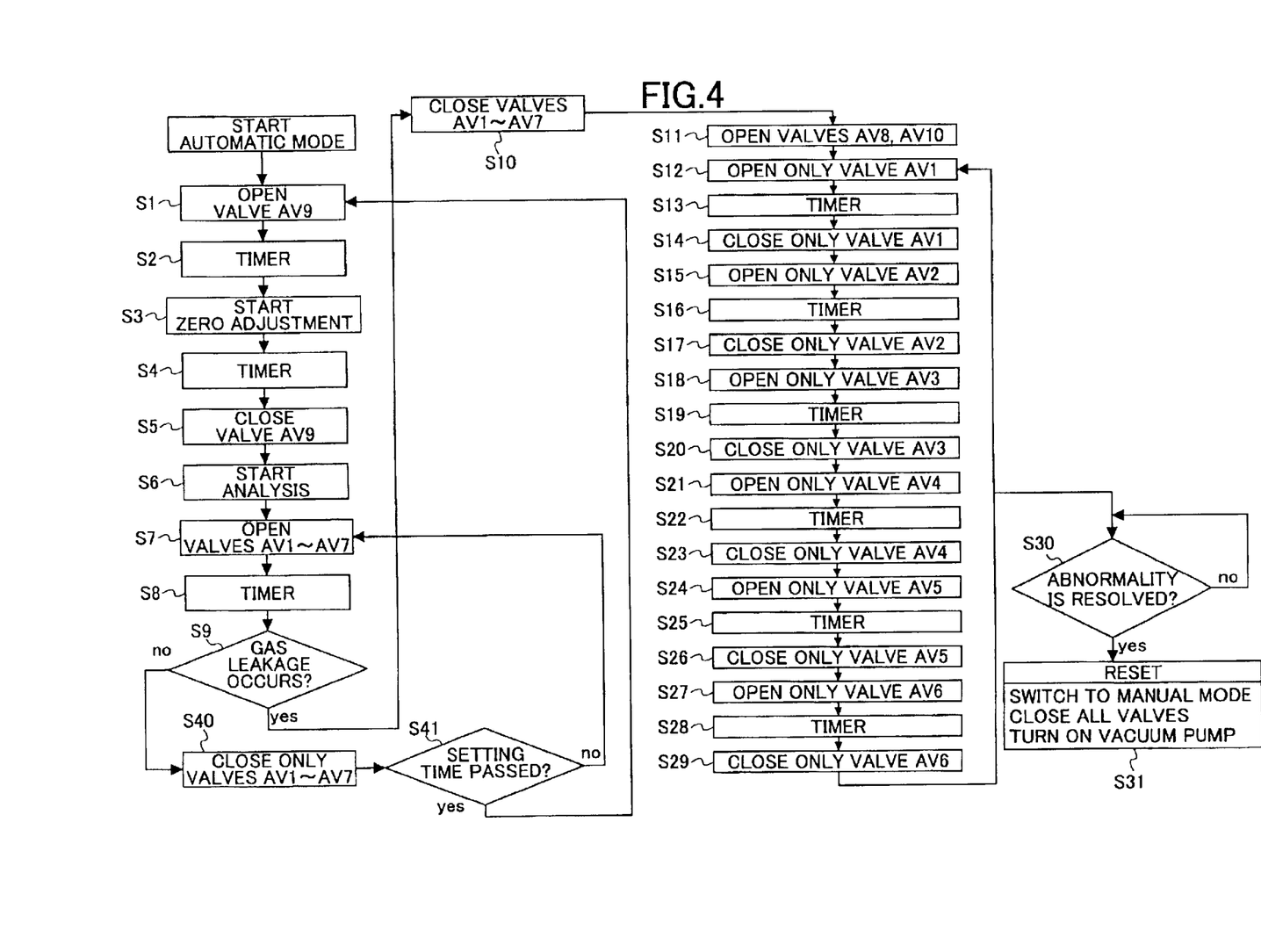
FIG. 4 is a flow chart showing the operation of the gas leakage detection system according to the first embodiment of the present invention.

In FIG. 4, in step S1, the air driving valve AV9 is opened by increasing the pressure of valve driving air supplied from the magnet valve 50 that is controlled by the controller 30. Next, in step S2, a timer included in the controller 30 clocks a time that is arbitrarily set between 30 seconds and 120 seconds. During this clocking, nitrogen for zero calibration is injected into the gas cell 40.

Then, in step S3, the controller 30 supplies the controller 42 via the additional function part 33 with a signal commanding start of zero adjustment, and the Fourier transform infrared spectrophotometer 28 starts the zero adjustment. Then, in step S4, the timer provided for the controller 30 clocks for 80 seconds. During the clocking, the Fourier transform infrared spectrophotometer 28 performs the zero adjustment. Then, in step S5, the air driving valve AV9 is closed by decreasing the pressure of the valve driving air supplied from the magnet valve 50 that is controlled by the controller 30.

Next, in step S6, the controller 30 supplies the controller 42 via the additional function part 33 with a signal commanding to start analysis of a gas that is sampled at the measurement point 36. Hence, the analysis of the sampled gas is started. Then, in step S7, the air driving valves AV1 through AV7 are opened by the magnet valves 51 through 57 that are supplied with valve switching signals by the controller 30. Hence, the gas sampled at the measurement point 36 is introduced to the gas cell 40 via the air driving valve AV7.

Here, in a case where a gas flows, at a flow rate outside a range of predetermined setting values, to at least one of the flowmeters 59 through 64 that are serially connected to the respective air driving valves AV1 through AV6, a flow rate abnormal signal is supplied to the controller 30. The controller 30 raises an alarm via the operation display monitor 31 so as to notify an operator of an abnormality in gas sampling.

Additionally, the system according to this embodiment can set the number of sampling points to an arbitrary number. That is, by supplying the switching signal to the air driving valves AV1 through AV6, the controller 30 opens/closes the air driving valves AV1 through AV6, and at the same time, automatically converts the detection concentration so that the detection concentration of each measuring gas is optimized according to the number of the valves that are opened/closed.

In step S8, the timer included in the controller 30 clocks a time. During the clocking, the Fourier transform infrared spectrophotometer 28 performs component analysis of the gas introduced to the gas cell 40. The concentration of the specific gas that is detected as a result of spectrum analysis is supplied to the controller 30.

Then, in step S9, by comparing the spectra stored in the controller 30 beforehand with the spectrum obtained through the analysis by the Fourier transform infrared spectrophotometer 28, it is determined whether or not the leakage of the specific gas occurs. In other words, in a case where the concentration of the detected specific gas is higher that the predetermined fixed value, it is determined that the specific gas leaks. Otherwise, it is determined that the leakage of the gas does not occur. The determination of the leakage may be performed continuously or at intervals that are arbitrarily set.

In step S9, in a case where it is determined that the specific gas leaks, the process proceeds to step S10. On the other hand, in a case where it is determined that the leakage of the gas does not occur, the process proceeds to step S41.

In step S41, the controller 30 determines whether or not six hours has passed. In a case where it is determined that six hours has passed, the process returns to step S1 via step S40. In a case where it is determined that six hours has not passed, the process returns to step S8. In step S40, the air driving valves AV1 through AV7 are closed by decreasing the pressure of the valve driving air supplied from the magnet valves 51 through 57 that are controlled by the controller 30.

On the other hand, also in step S10, the air driving valves AV1 through AV7 are closed by reducing the pressure of the valve driving air supplied from the magnet valves 51 through 57 that are controlled by the controller 30. Then, in step S11, the air driving valve AV8 is opened by the magnet valve 70 supplied with the valve switching signal by the controller 30. Similarly, the air driving valve AV10 is opened by the magnet valve 49 supplied with the valve switching signal by the controller 30. By opening the air driving valve AV10 as mentioned above, nitrogen for diluting exhaust is supplied to the exhaust pipe 68. Hence, even in a case where a toxic gas leaks, the leaking gas is diluted, and safety is secured.

Then, in step S12, only the air driving valve AV1 is opened by the magnet valve 5l supplied with the valve switching signal by the controller 30. Hence, only a gas that is sampled at the sample port connected to the air driving valve AV1 is introduced to the gas cell 40 via the air driving valve AV8. In step S13, the controller 30 clocks 60 seconds. During the clocking, the Fourier transform infrared spectrophotometer 28 performs the component analysis of the gas that is introduced to the gas cell 40.

Here, in a case where the controller 30 determines that the concentration of the specific gas is higher than the predetermined fixed value in a result of the spectrum analysis in step S13, the controller 30 supplies the operation display monitor 31 with a signal indicating that the specific gas is leaking from the sample port connected to the air driving valve AV1. Hence, the kind of the leaking gas and the leaking place are displayed on the operation display monitor 31. In this case, by attaching a buzzer or the like to the operation display monitor 31, it is possible to raise an alarm by sounding a buzzer according to the above-mentioned signal. It should be noted that such an alarm can be similarly applied to all cases where the leakage of a gas is detected.

Next, in step S14, the air driving valve AV1 is closed by reducing the pressure of the valve driving air supplied from the magnet valve 50 that is controlled by the controller 30. At the same time, the pump 58 exhausts the gas in the gas cell 40.

In the following, similarly, in step S15, only the air driving valve AV2 is opened by the magnet valve 52 supplied with the valve switching signal from the controller 30. Hence, only the gas that is sampled at the sample port connected to the air driving valve AV2 is introduced to the gas cell 40 via the air driving valve AV8. In step S16, the controller 30 clocks 60 seconds. During the clocking, the Fourier transform infrared spectrophotometer 28 performs the component analysis of the above-mentioned gas that is introduced to the gas cell 40.

In a case where the controller 30 determines that the concentration of the specific gas is higher than the predetermined fixed value from a result of the spectrum analysis in step S16, the controller 30 supplies the operation display monitor 31 with a signal indicating that the specific gas is leaking from the sample port connected to the air driving valve AV2. Hence, the kind of the leaking gas and the leaking place are displayed on the operation display monitor 31. Next, in step S17, the air driving valve AV2 is closed by reducing the pressure of the valve driving air supplied from the magnet valve 52 that is controlled by the controller 30. At the same time, the pump 58 exhausts the gas in the gas cell 40.

In step S18, only the air driving valve AV3 is opened by the magnet valve 53 supplied with the valve switching signal by the controller 30. Hence, only a gas that is sampled at the sample port connected to the air driving valve AV3 is introduced to the gas cell 40 via the air driving valve AV8. In step S19, the controller 30 clocks 60 seconds. During the clocking, the Fourier transform infrared spectrophotometer 28 performs the component analysis of the above-mentioned gas that is introduced to the gas cell 40.

In a case where the controller 30 determines that the concentration of the specific gas is higher than the predetermined fixed value from a result of the spectrum analysis in step S19, the controller 30 supplies the operation display monitor 31 with a signal indicating that the specific gas is leaking from the sample port connected to the air driving valve AV3. Hence, the kind of the leaking gas and the leaking place are displayed on the operation display monitor 31. Next, in step S20, the air driving valve AV3 is closed by reducing the pressure of the valve driving air supplied from the magnet valve 52 that is controlled by the controller 30. At the same time, the pump 58 exhausts the gas in the gas cell 40.

In step S21, only the air driving valve AV4 is opened by the magnet valve 54 supplied with the valve switching signal by the controller 30. Hence, only a gas that is sampled at the sample port connected to the air driving valve AV4 is introduced to the gas cell 40 via the air driving valve AV8. In step S22, the controller 30 clocks 60 seconds. During the clocking, the Fourier transform infrared spectrophotometer 28 performs the component analysis of the above-mentioned gas that is introduced to the gas cell 40.

In a case where the controller 30 determines that the concentration of the specific gas is higher than the predetermined fixed value from a result of the spectrum analysis in step S22, the controller 30 supplies the operation display monitor 31 with a signal indicating that the specific gas is leaking from the sample port connected to the air driving valve AV4. Hence, the kind of the leaking gas and the leaking place are displayed on the operation display monitor 31. Next, in step S23, the air driving valve AV4 is closed by reducing the pressure of the valve driving air supplied from the magnet valve 54 that is controlled by the controller 30. At the same time, the pump 58 exhausts the gas in the gas cell 40.

In step S24, only the air driving valve AV5 is opened by the magnet valve 55 supplied with the valve switching signal by the controller 30. Hence, only a gas that is sampled at the sample port connected to the air driving valve AV5 is introduced to the gas cell 40 via the air driving valve AV8. In step S25, the controller 30 clocks 60 seconds. During the clocking, the Fourier transform infrared spectrophotometer 28 performs the component analysis of the above-mentioned gas that is introduced to the gas cell 40.

In a case where the controller 30 determines that the concentration of the specific gas is higher than the predetermined fixed value from a result of the spectrum analysis in step S25, the controller 30 supplies the operation display monitor 31 with a signal indicating that the specific gas is leaking from the sample port connected to the air driving valve AV5. Hence, the kind of the leaking gas and the leaking place are displayed on the operation display monitor 31. Next, in step S26, the air driving valve AV5 is closed by reducing the pressure of the valve driving air supplied from the magnet valve 55 that is controlled by the controller 30. At the same time, the pump 58 exhausts the gas in the gas cell 40.

In step S27, only the air driving valve AV6 is opened by the magnet valve 56 supplied with the valve switching signal by the controller 30. Hence, only a gas that is sampled at the sample port connected to the air driving valve AV6 is introduced to the gas cell 40 via the air driving valve AV8. In step S28, the controller 30 clocks 60 seconds. During the clocking, the Fourier transform infrared spectrophotometer 28 performs the component analysis of the above-mentioned gas that is introduced to the gas cell 40.

In a case where the controller 30 determines that the concentration of the specific gas is higher than the predetermined fixed value from a result of the spectrum analysis in step S28, the controller 30 supplies the operation display monitor 31 with a signal indicating that the specific gas is leaking from the sample port connected to the air driving valve AV6. Hence, the kind of the leaking gas and the leaking place are displayed on the operation display monitor 31. Next, in step S29, the air driving valve AV6 is closed by reducing the pressure of the valve driving air supplied from the magnet valve 56 that is controlled by the controller 30. At the same time, the pump 58 exhausts the gas in the gas cell 40.

Then, in order to investigate whether there is any change with time such as spreading of the gas leakage, the process returns to step S12, and steps S12 through S29 are repeated.

On the other hand, in step S30, it is determined whether or not an abnormal state in which the leakage of the gas occurs is resolved and returned to a normal state. In a case where it is determined that the abnormal state is not resolved, the process cannot proceed to step S31. In a case where it is determined that the abnormality is resolved in step S30, the process proceeds to step S31. Here, the determination in step S30 is made based on whether or not the concentration of the gas obtained as a result of the spectrum analysis is lower than the above-mentioned fixed value. In other words, it is determined that the abnormality is resolved in a case where the concentration of the gas that is determined to be leaking is lower than the fixed value.

In step S31, the gas leakage detection system assumes a measurement waiting state when an operator performs a reset operation. That is, the controller 30 switches the gas leakage detection system to the manual mode in which all the operations are manually performed, and closes all the air driving valves AV1 through AV10. Additionally, at this moment, the pump 58 exhausts the gas included in the gas cell 40.

Further, in step S7, all the flowmeters 59 through 64 are set so as to pass the same quantity of the gas, and the gases that are sampled at the plurality of sample ports included in the measurement point 36 are simultaneously introduced to the gas cell 40 via the air driving valve AV7. Consequently, it is possible to constantly detect and alarm for the leakage of the gas with high accuracy. It should be noted that, depending on a method of data processing, there is a possibility that the accuracy of the measured values of the concentration are deteriorated due to bias of the flow rates, in a case where the flow rates of the gases flowing through the flowmeters 59 through 64 are not even.

Then, in a case where the gases that are sampled at the plurality of sample ports are simultaneously introduced to the gas cell 40, after the gas leakage is detected and the alarm is raised as mentioned above, by switching the air driving valves AV1 through AV8, the gas that is sampled at the individual sample port is automatically and sequentially introduced to the gas cell 40. Accordingly, it is possible to specify the place where the predetermined gas leaks.

[Second Embodiment]

Figure 5:
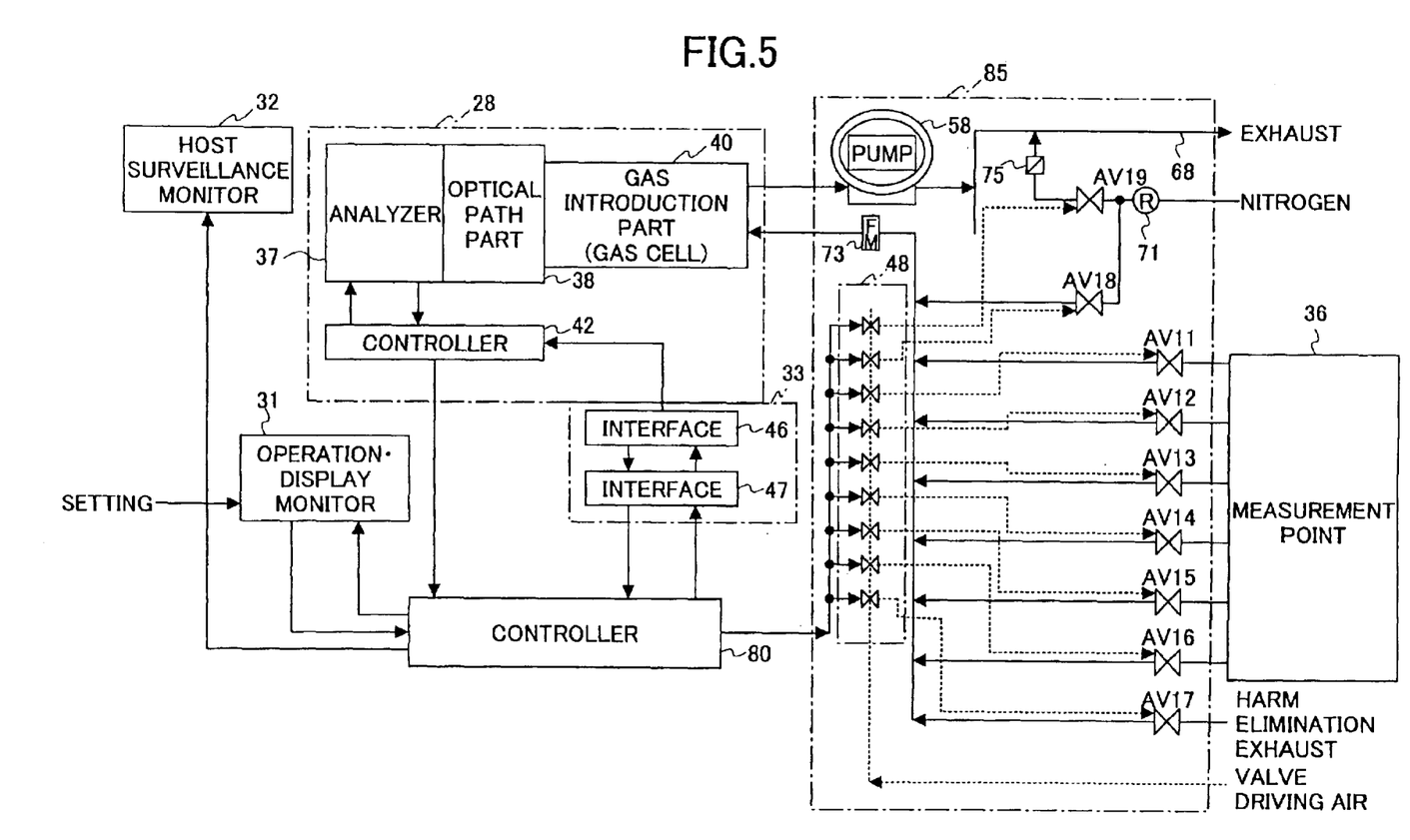
FIG. 5 is a block diagram of a gas leakage detection apparatus provided to a gas leakage detection system according to a second embodiment of the present invention.

FIG. 5 is a block diagram of a gas leakage detection apparatus installed in a gas leakage detection system according to a second embodiment of the present invention. The gas leakage detection apparatus shown in FIG. 5 has a construction similar to that of the gas leakage detection apparatus according to the first embodiment shown in FIG. 3. However, the difference exists in the construction of a valve switch part 85.

The valve switch part 85 includes air driving valves AV11 through AV19, a pressure regulator 71, a flowmeter (FM) 73, and a stop valve 75. The flowmeter 73 is connected to the gas introduction part (gas cell) 40. Each of the air driving valves AV11 through AV18 is connected to the flowmeter 73. The air driving valve AV19 is connected to the exhaust pipe 68 via the stop valve 75. In addition, input ports of the air driving valves AV18 and AV19 are both connected to the pressure regulator 71. Then, an input port of the air driving valve AV17 is connected to the sample port 27 attached to process exhaust opening of the harm eliminating box 9.

Figure 6:
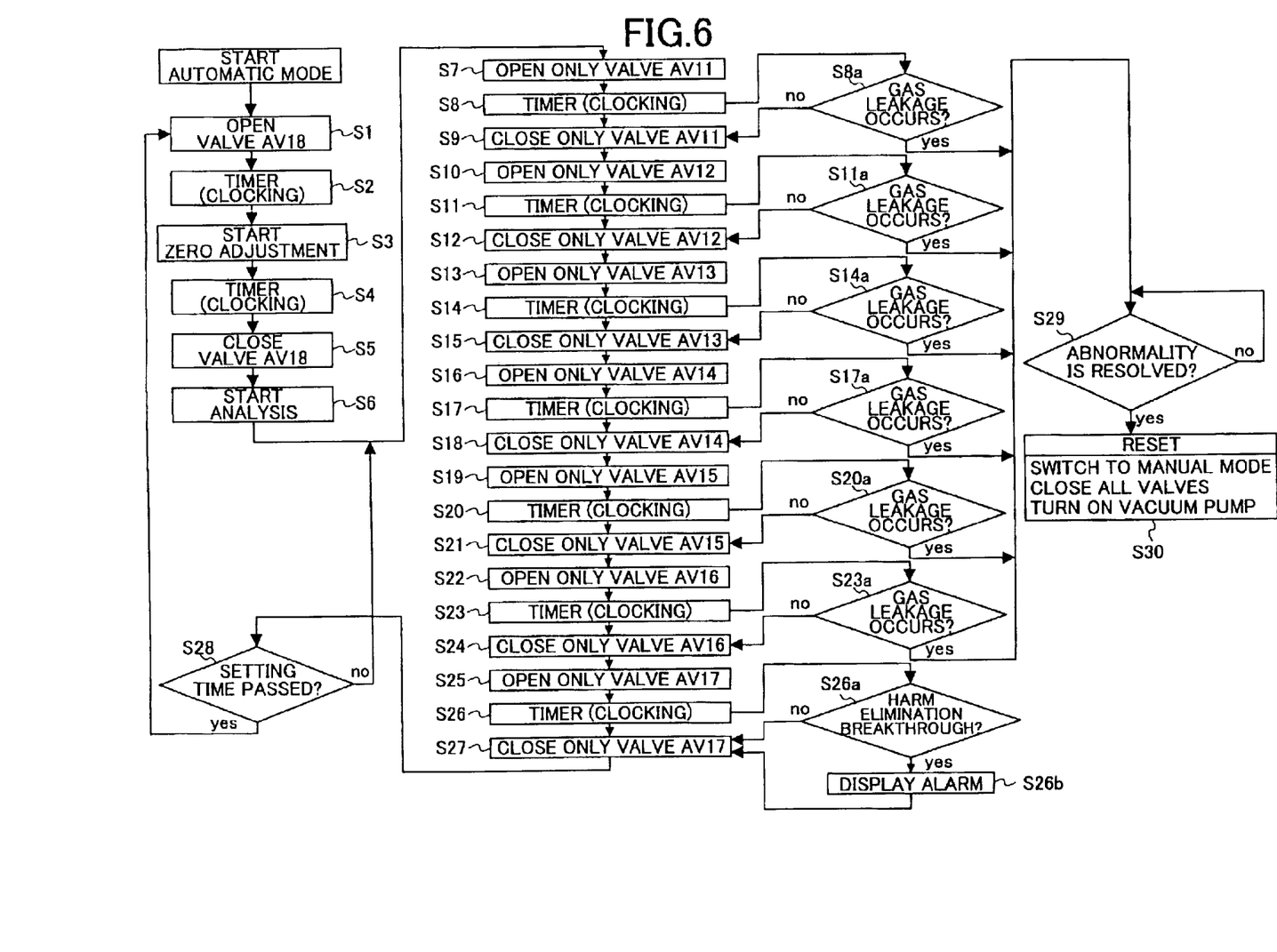
FIG. 6 is a flow chart showing the operation of the gas leakage detection system according to the second embodiment of the present invention.

Next, a description will be given of the operation of the gas leakage detection apparatus according to this embodiment, by referring to FIG. 6. It should be noted that, the operation described in the following is the operation when the automatic mode is set, however, this operation can also be carried out in the manual mode.

First, in step S1, the air driving valve AV18 is opened by increasing the pressure of the valve driving air by a controller 80. Next, in step S2, the controller 80 clocks a time that is arbitrarily set. During this clocking, nitrogen for the zero calibration is injected in to the gas cell 40.

Then, in step S3, the controller 80 supplies the controller 42 via the additional function part 33 with a signal commanding the start of the zero adjustment, and the Fourier transform infrared spectrophotometer 28 starts the zero adjustment. Then, in step S4, the controller 80 clocks the predetermined time, and the Fourier transform infrared spectrophotometer 28 performs the zero adjustment during the clocking. Then, in step S5, the air driving valve AV18 is closed by reducing the pressure of the valve driving air by the controller 80.

Next, in step S6, the controller 80 supplies the controller 42 via the additional function part 33 with a signal commanding the start of the analysis of a gas that is sampled at the measurement point 36, and hence, the analysis of the gas is started. Then, in step S7, only the air driving valve AV11 is opened by the controller 80.

Hence, the gas that is sampled at the measurement point 36 is introduced to the gas cell 40 via the air driving valve AV11.

Here, in a case where the gas flows to the flowmeter 73 at a flow rate outside a range of predetermined setting values, based on the flow rate abnormal signal supplied from the flowmeter, the controller 80 raises an alarm via the operation display monitor 31 and announces the abnormality in the gas sampling.

Next, in step S8, the controller 80 clocks the predetermined time. During the clocking, the Fourier transform infrared spectrophotometer 28 performs the component analysis of the gas that is introduced to the gas cell 40. Then, in step S8a, it is determined whether or not the leakage of the specific gas of which spectrum is stored in the controller 80 beforehand occurs, by referring to the detected concentration of the above-mentioned specific gas, continuously or at intervals that are arbitrarily set.

In a case where it is determined that the leakage of the above-mentioned specific gas occurs, the process proceeds to step S29. In a case where it is determined that the leakage does not occur, the process proceeds to step S9. It should be noted that, in step S29, whether or not the abnormality is resolved is determined by whether or not the concentration of the gas that is obtained as a result of the spectrum analysis is lower than the predetermined value. In a case where it is determined that the abnormality is resolved, the process proceeds to step S30.

In step S30, the gas leakage detection system assumes a measurement waiting state when an operator performs the reset operation. That is, the controller 80 switches the gas leakage detection system to the manual mode in which all the operations are manually performed, and closes all the air driving valves AV11 through AV19. Additionally, at this moment, the pump 58 exhausts the gas included in the gas cell 40.

On the other hand, in a case where the process proceeds to step S9, the air driving valve AV11 is closed by reducing the pressure of the valve driving air by the controller 80. Then, from step S10 to step S24, with respect to the air driving valves AV12 through AV16, the operation from step S7 to step S9 is successively repeated. Then, in step S25, the controller 80 opens only the air driving valve AV17. Hence, the gas that is sampled at the sample port 27 is introduced to the gas cell 40 via the air driving valve AV17 and the flowmeter 73.

Here, in a case where the gas flows to the flowmeter 73 at a flow rate outside the range of predetermined setting values, based on the flow rate abnormality signal supplied from the flowmeter, the controller 80 raises an alarm via the operation display monitor 31 and announces the abnormality in the gas sampling.

Next, in step S26, the controller 80 clocks the predetermined time. During the clocking, the Fourier transform infrared spectrophotometer 28 performs the component analysis of the gas that is introduced to the gas cell 40. Then, in step S26a, by referring to the detected concentration of the above-mentioned specific gas, it is determined continuously or at intervals that are arbitrarily set whether or not breakthrough occurs in the harm eliminator.

In a case where it is determined that the breakthrough occurs, the process proceeds to step S26b, the operation display monitor 31 displays and alarms that harm elimination breakthrough occurs, and the process proceeds to step S27. On the other hand, in step S26a, in a case where it is determined that the harm elimination breakthrough does not occur, the process proceeds to step S27. In step S27, the air driving valve AV17 is closed by reducing the pressure of the valve driving air by the controller 80.

Then, in step 28, the controller 80 determines whether or not the predetermined time has passed. In a case where it is determined that the predetermined time has passed, the process proceeds to step S1. In a case where it is determined that the predetermined time has not passed, the process returns to step S7.

In addition, as a result of the above-mentioned spectrum analysis, in a case where it is determined that the concentration of the specific gas is higher than the predetermined value, the controller 80 supplies the operation display monitor 31 with a signal specifying the sample port at which the specific gas is sampled. Hence, the operation display monitor 31 displays the kind of the leaking gas and the leaking place. In this case, by attaching a buzzer or the like to the operation display monitor 31, it is also possible to sound the buzzer or the like according to the above-mentioned signal so as to raise an alarm. It should be noted that such an alarm can be similarly applied to all cases where the leakage of a gas is detected.

As described above, according to the gas leakage detection system of this embodiment, the leakage of the specific gas is detected by successively introducing, to the Fourier transform infrared spectrophotometer 28, the gases that are sampled at the measurement point 36 and the exhaust opening of the harm eliminating box 9. Thus, it is possible to promptly specify the kind of leaking gas and the leaking place with a simple construction.

Here, since the sample port 27 connected to the air driving valve AV17 is attached to an exhaust pipe connected to an exhaust opening of an exhaust gas harm eliminator that is filled with a medical agent or the like, it is possible to detect the saturation of the medical agent. It is useful to detect the breakthrough point by the method as mentioned above, since a problem that the harm elimination cannot be performed occurs at the breakthrough point at which the medical agent is saturated in the exhaust gas harm eliminator. However, the detection and alarm of the breakthrough point in the harm eliminator are performed in a form distinct from that of the detection and alarm of the gas leakage.

[Third Embodiment]

Figure 7:
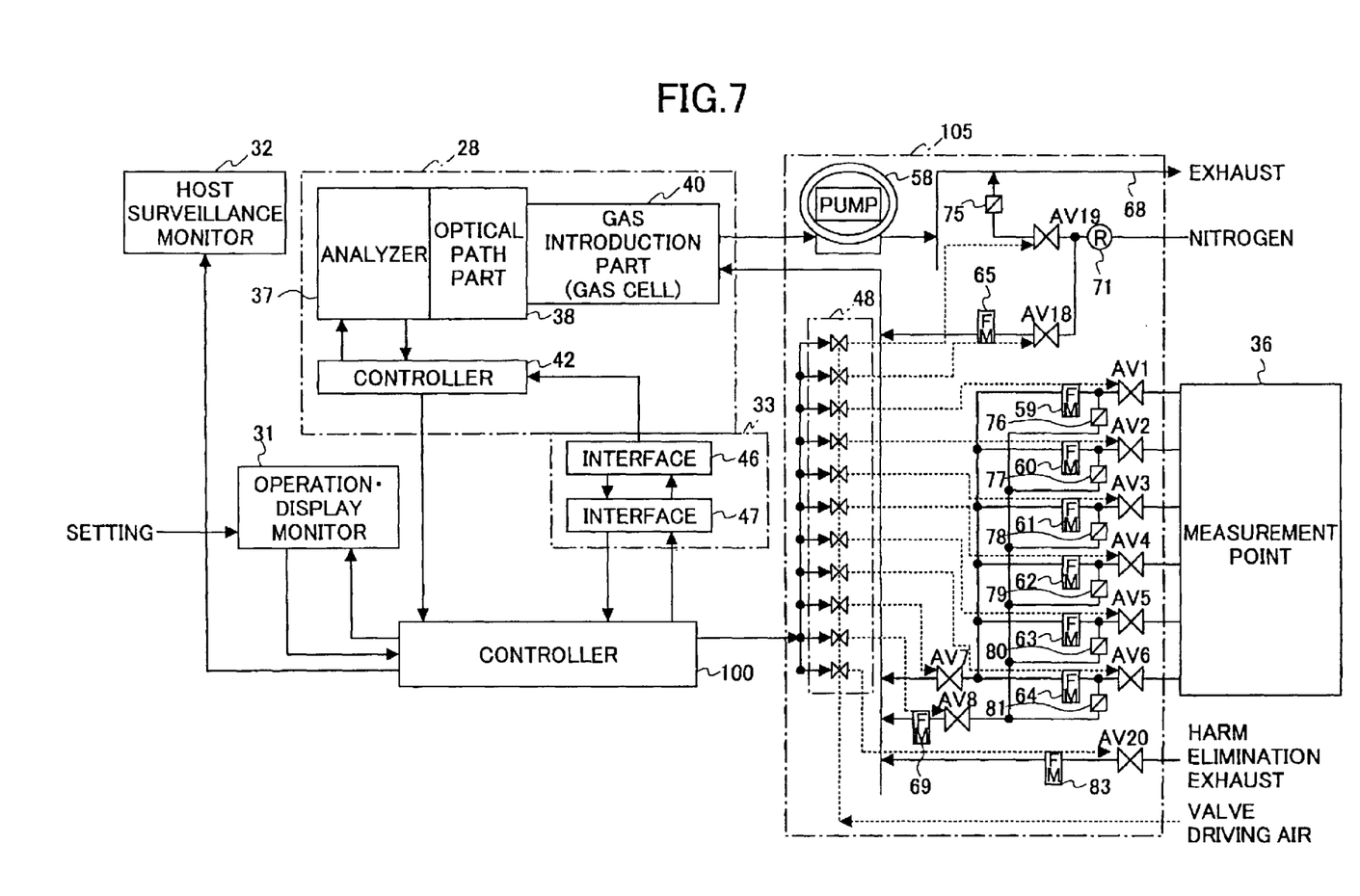
FIG. 7 is a block diagram of a gas leakage detection apparatus provided to a gas leakage detection system according to a third embodiment of the present invention.

FIG. 7 is a block diagram of a gas leakage detection apparatus installed in a gas leakage detection system according to a third embodiment of the present invention. The gas leakage detection apparatus shown in FIG. 7 has a construction similar to that of the gas leakage detection apparatus according to the first embodiment shown in FIG. 3. However, the difference exists in the construction of a valve switch part 105.

The valve switch part 105 includes a flowmeter 83 and an air driving valve AV20. An input port of the air driving valve AV20 is connected to the sample port 27 attached to the process exhaust opening of the harm eliminating box 9, and an output port is connected to the gas cell 40 via the flowmeter 83.

A description will be given of the operation of the gas leakage detection apparatus according to this embodiment, which has the construction as described above, by referring to FIG. 8. It should be noted that the operation described in the following is the operation when the automatic mode is set, however, this operation can also be carried out in the manual mode.

Figure 8:
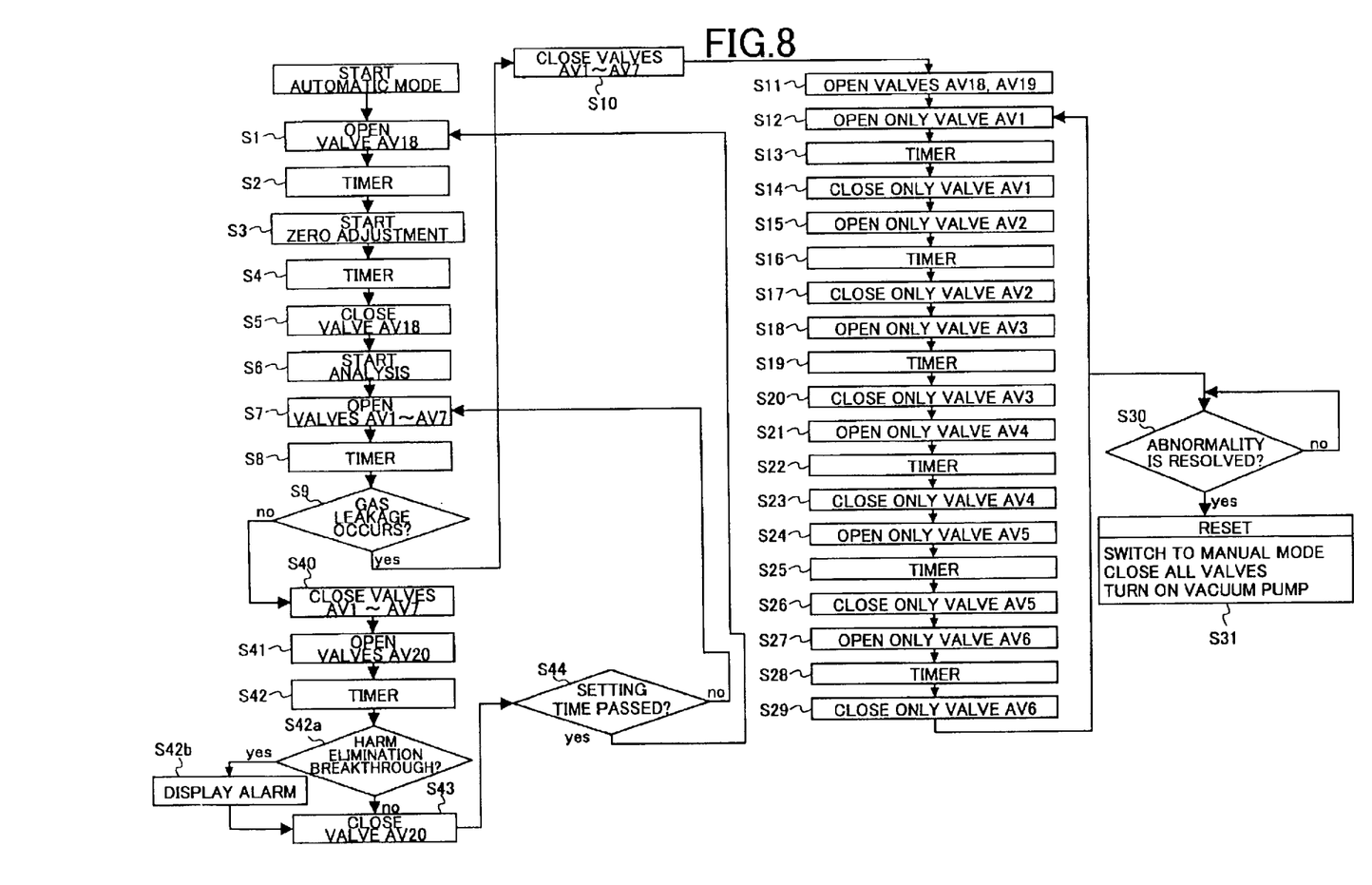
FIG. 8 is a flow chart showing the operation of the gas leakage detection system according to the third embodiment of the present invention.

In the gas leakage detection apparatus according to this embodiment, process from step S1 to step S31, process of step S40 and process of step S44 are similar to those of the gas leakage detection apparatus according to the above-mentioned first embodiment. However, the difference exists in the process from step S41 to step S43. In the following, a description will be given of the difference.

In step S41, a controller 100 opens the air driving valve AV20. Hence, a gas that is sampled from exhaust of the harm eliminating box 9 at the sample port 27 connected to the air driving valve AV20 is introduced to the gas cell 40. In step S42, a timer incorporated in the controller 100 clocks the predetermined time. During the clocking, the Fourier transform infrared spectrophotometer 28 performs the component analysis of the gas that is introduced to the gas cell 40.

Then, in step S42a, as a result of the spectrum analysis in step S42, in a case where the concentration of the specific gas is higher than the predetermined value, the controller 100 determines that the harm elimination breakthrough occurs. In a case where it is determined that the harm elimination breakthrough occurs, the process proceeds to step S42b, and the controller 100 supplies the operation display monitor 31 with a signal indicating that the harm elimination breakthrough occurs. Hence, the operation display monitor 31 displays the occurrence of the harm elimination breakthrough and the kind of gas that causes the breakthrough. In this case, by attaching a buzzer or the like to the operation display monitor 31, it is possible to raise an alarm by sounding the buzzer or the like so as to indicate that the harm eliminating box 9 is abnormal. On the other hand, in step S42a, in a case where it is determined that the harm elimination breakthrough does not occur, the process proceeds to step S43.

In step S43, the air driving valve AV20 is closed by reducing the pressure of the valve driving air by the controller 100. At the same time, the pump 58 exhausts the gas in the gas cell 40, and the process proceeds to step S44.

As described above, according to the gas leakage detection apparatus of this embodiment, the effect similar to the gas leakage detection apparatus according to the above-mentioned first embodiment is obtained. At the same time, it is possible to detect, with good accuracy, the saturation of the medical agent or the like in the harm eliminating box 9 that is filled with the medical agent or the like.

According to the gas leakage detection system of this embodiment, it is possible to simultaneously detect the leakage of many kinds of gases by kind. In addition, it is possible to detect the leakage of the gases at many places by a vacuum measurement method by a single Fourier transform infrared spectrophotometer 28. Thus, it is not necessary to arrange a gas detector for each place where leakage is possible. Therefore, it is possible to drastically reduce the control items of the gas leakage detection system.

Additionally, in a case where a new gas becomes the detection target, all that is required is to store the spectrum of the gas in the Fourier transform infrared spectrophotometer 28. Thus, it is possible to simply perform the setting of the gas leakage detection system. Further, in the spectrum analysis by the Fourier transform infrared spectrophotometer 28, the interference between the gas that is the detection target and another gas hardly occurs. Accordingly, it is possible to avoid the occurrence of problems such as erroneously detecting the leakage of a gas.

In each of the above-mentioned embodiments, the gas leakage detection apparatus 25 detects the gas leakage from apparatuses arranged around the semiconductor manufacturing apparatus housing (M/C) 5, in addition to detecting the gas leakage from the semiconductor manufacturing apparatus. Thus, in each of the above-mentioned embodiments, the leakage detection apparatus 25 is located in a position different from that of the semiconductor manufacturing apparatus housing (M/C) 5. However, the gas leakage detection apparatus 25 according to the present invention may be incorporated in the semiconductor manufacturing apparatus housing (M/C) 5 as a part of the semiconductor manufacturing apparatus, or attached to the semiconductor manufacturing apparatus housing (M/C) 5. In this case, the gas leakage detection apparatus 25 may detect only the gas leakage in the semiconductor manufacturing apparatus housing (M/C) 5, or detect also the gas leakage from another peripheral apparatus.

As the above-mentioned embodiments, when the leakage of the specific gas is detected in a case where at least one specific gas is included in the gas as a result of analyzing the components of the sampled gas, it is possible to detect the leakage of a plurality of specific gases by type with good accuracy. Accordingly, it is possible to realize a highly accurate gas leakage detection system while reducing the scale of the system.

In addition, in a case where a harmful substance is included in gases exhausted from a harm eliminating means equal to or more than a predetermined quantity, by determining that the harm eliminating means is abnormal, it is possible to detect the breakthrough point of the harm eliminating means with good accuracy. Hence, the reliability of the harm eliminating means can be increased. Further, by analyzing the component of the gases by a Fourier transform infrared spectrophotometer, it is possible to perform analysis with good accuracy. Thus, the reliability of the gas leakage detection system can be ensured.

Additionally, by introducing nitrogen gas to the Fourier transform infrared spectrophotometer and performing the zero calibration at predetermined intervals for the zero calibration of the Fourier transform infrared spectrophotometer, it is possible to maintain the accuracy of the analysis by the Fourier transform infrared spectrophotometer. Hence, it is possible to further increase the reliability of the operation of the gas leakage detection system.

Furthermore, in a case where the gases include at least one specific gas with quantity equal to or more than the predetermined quantity as a result of the analysis, by successively analyzing the gas supplied from each gas sampling part, it is possible to specify the place where the specific gas is leaking. Hence, it is possible to promptly recognize the leaking state of the gas.

Additionally, by providing a flow rate regulating means for regulating the flow rate of the gases flowing from the gas sampling means to the analyzer, it is possible to increase the accuracy of the analysis by the analyzing means. Hence, it is possible to further increase the accuracy of the gas leakage detection system. In addition, by raising an alarm when the gases are supplied to the analyzing means at a flow rate outside a predetermined range, it is possible to maintain the accuracy of the analysis by the analyzing means. Thus, it is possible to increase the reliability of the operation of the gas leakage detection system.

Further, in a case where the quantity of the predetermined specific gas is included in the gas equal to or more than a predetermined quantity as a result of the analysis, it is possible to avoid the risk due to the leakage of the specific gas by diluting the predetermined specific gas that is exhausted. Hence, it is possible to obtain a gas leakage detection system taking safety into consideration. Additionally, by outputting a signal indicating the leakage of the specific gas included with quantity equal to or more than the predetermined quantity, it is possible to transmit a signal indicating the leakage of the specific gas to an upper machine such as a host computer, for example. Thus, it is possible to increase the flexibility of measures relating to the gas leakage.

Furthermore, by outputting a signal indicating that the harm eliminating means is abnormal, it is possible to transmit the signal indicating the abnormality of the harm eliminating means to the upper machine. Accordingly, it is possible to increase the flexibility of measures relating to the abnormality of the harm eliminator.

What is claimed is:

1. A gas leakage detection system detecting leakage of a plurality of kinds of specific gases, comprising:

analyzing means for analyzing components of a sampled gas; and determining means for determining that at least one kind of the specific gases leaks when the one kind of the specific gases is included in the sampled gas equal to or more than a predetermined quantity, as a result of analysis by said analyzing means.

2. The gas leakage detection system as claimed in claim 1, comprising:

sampling means for sampling gases exhausted from harm eliminating means for eliminating a harmful substance included in the plurality of kinds of specific gases, wherein the determining means determines that said harm eliminating means is abnormal, in a case where the harmful substance is included in the gases exhausted from said harm eliminating means equal to or more than the predetermined quantity.

3. The gas leakage detection system as claimed in claim 1 or 2, wherein the analyzing means is a Fourier transform infrared spectrophotometer.

4. The gas leakage detection system as claimed in claim 2, wherein the determining means outputs a signal indicating that the harm eliminating means is abnormal, when determining that the harm eliminating means is abnormal.

5. The gas leakage detection system as claimed in claim 3, further comprising:

nitrogen gas supplying means for introducing a nitrogen gas to the Fourier transform infrared spectrophotometer for zero calibration of the Fourier transform infrared spectrophotometer; and controlling means for controlling said nitrogen gas supplying means so that the zero calibration is performed at predetermined intervals.

6. The gas leakage detection system as claimed in claim 1, comprising:
sampling means for individually sampling gases from a plurality of sampling locations,
wherein the sampled gases are successively supplied to the analyzing means.

7. The gas leakage detection system as claimed in claim 5, wherein the sampling means includes flow rate regulating means for regulating flow rate of a gas flowing from at least one of the sampling locations to the analyzing means.

8. The gas leakage detection system as claimed in claim 1, comprising:
sampling means for individually sampling gases from the plurality of sampling locations; and
controlling means for controlling the gases sampled from the plurality of sampling locations to be individually and successively supplied to the analyzing means, in a case where at least one kind of the specific gases is included in the gas equal to or more than a predetermined quantity, as a result of the analysis by the analyzing means, when the gases sampled from the plurality of sampling locations are simultaneously supplied to the gas analyzing means.

9. The gas leakage detection system as claimed in claim 1, further comprising:
alarming means for raising an alarm when a flow rate of the gas supplied to the analyzing means is beyond a predetermined range.

10. The gas leakage detection system as claimed in claim 1, further comprising:
diluting means for diluting a predetermined kind of the specific gases exhausted from the analyzing means, in a case where the predetermined kind of the specific gases is included in the sampled gas equal to or more than the predetermined quantity, as a result of the analysis by the analyzing means.

11. The gas leakage detection system as claimed in clam 1, wherein the determining means outputs a signal indicating leakage of one kind of the specific gases determined to be leaking, when determining that at least the one kind of the specific gases leaks.

12. A gas leakage detection method of detecting leakage of a plurality of kinds of specific gases, comprising:
an analyzing step of analyzing components of sampled gases;
a step of determining whether or not at least one kind of the specific gases is included in the sampled gases equal to or more than a predetermined quantity; and
a step of determining that one kind of the specific gases leaks, in a case where it is determined that at least the one kind of the specific gases is included equal to or more than the predetermined quantity.

13. A gas leakage detection method of monitoring an operating state of a harm eliminating means eliminating a harmful substance included in a plurality of kinds of specific gases that leak, comprising:
an analyzing step of analyzing components of gases exhausted from the harm eliminating means;
a step of determining whether or not the gases exhausted from the harm eliminating means include at least one kind of the specific gases equal to or more than a predetermined quantity; and
a step of determining that abnormality occurs in the harm eliminator, in a case where it is determined that the gases exhausted from the harm eliminating means include at least the one kind of the specific gases equal to or more than the predetermined quantity.

14. The gas leakage detection method as claimed in claim 12 or 13, wherein the analyzing step is performed by using a Fourier transform infrared spectrophotometer.

15. The gas leakage detection method as claimed in claim 14, further comprising:
a step of performing zero calibration of the Fourier transform infrared spectrophotometer at predetermined intervals; and
a step of supplying a nitrogen gas to the Fourier transform infrared spectrophotometer in the zero calibration.

16. The gas leakage detection method as claimed in claim 12, further comprising:
a step of sampling gases at a plurality of sampling locations; and
a step of simultaneously analyzing the gases sampled at the plurality of sampling locations.

17. The gas leakage detection method as claimed in claim 16, comprising:
a step of individually and successively analyzing the gases sampled at the plurality of sampling locations, in a case where the sampled gases include at least one of the specific gases equal to or more than the predetermined quantity, as a result of the analysis.

18. The gas leakage detection method as claimed in claim 12 or 13, further comprising:
a step of regulating quantity of the gases to be analyzed to a predetermined value.

19. The gas leakage detection method as claimed in claim 12 or 13, further comprising:
a step of raising an alarm when a flow rate of the gases to be analyzed exceeds a predetermined value.

20. The gas leakage detection method as claimed in claim 12 or 13, further comprising:
a step of diluting a predetermined kind of the specific gas exhausted after the analysis, in a case where the sampled gases include the predetermined kind of the specific gas equal to or more than a predetermined quantity.

21. A semiconductor manufacturing apparatus using a plurality of kinds of specific gases, comprising:
a semiconductor manufacturing apparatus housing;
sampling means for sampling gases exhausted from said semiconductor manufacturing apparatus housing;
analyzing means for analyzing components of the sampled gases;
determining means for determining that at least one kind of the specific gases leaks when the sampled gases include the one kind of the specific gases equal to or more than a predetermined quantity, as a result of the analysis by said analyzing means; and
a gas leakage detection function of detecting leakage of the plurality of kinds of specific gases.

22. The semiconductor manufacturing apparatus as claimed in claim 21, wherein the analyzing means is a Fourier transform infrared spectrophotometer.

23. The semiconductor manufacturing apparatus as claimed in claim 22, further comprising:
nitrogen gas supplying means for introducing a nitrogen gas to the Fourier transform infrared spectrophotometer for zero calibration of the Fourier transform infrared spectrophotometer; and
control means for controlling said nitrogen gas supplying means so that the zero calibration is performed at predetermined intervals.

24. The semiconductor manufacturing apparatus as claimed in claim 21, wherein the sampling means individually samples gases from a plurality of sampling locations and successively supplies the sampled gases to the analyzing means.

25. The semiconductor manufacturing apparatus as claimed in claim 21, wherein the sampling means individually samples gases from a plurality of sampling locations, and said semiconductor manufacturing apparatus comprises:

control means for controlling the gases sampled from the plurality of sampling locations to be individually and successively supplied to the analyzing means, in a case where the gases include at least one kind of the specific gases equal to or more than the predetermined quantity, as a result of the analysis by the analyzing means when the gases sampled from the plurality of sampling locations are simultaneously supplied to the gas analyzing means.

26. The semiconductor manufacturing method as claimed in claim 25, wherein the sampling means includes flow rate regulating means for regulating a flow rate of the gases flowing from at least one of the sampling locations to the analyzing means.

27. The semiconductor manufacturing apparatus as claimed in claim 21, further comprising:

alarm means for raising an alarm when a flow rate of the gases supplied to the analyzing means is beyond a predetermined range.

28. The semiconductor manufacturing apparatus as claimed in claim 21, further comprising:

diluting means for diluting a predetermined kind of the specific gas exhausted from the analyzing means, in a case where the sampled gases include the predetermined kind of the specific gas equal to or more than the predetermined quantity as a result of the analysis by the analyzing means.

29. The semiconductor manufacturing apparatus as claimed in claim 21, wherein when the determining means determines that at least one kind of the specific gases leaks, the determining means outputs a signal indicating leakage of the one kind of the specific gases determined to be leaking.

* * * * *